United States Patent [19]

Faraci et al.

[11] 4,066,713

[45] Jan. 3, 1978

[54] PROCESS FOR THE ADDITION OF ORGANIC ACIDS TO ACETYLENIC COMPOUNDS CONTAINED IN INORGANIC OR ORGANIC HYDROCARBON STREAMS

[75] Inventors: Rocco Faraci; Carlo Rescalli; Stefano Catini, all of San Donato (Milan), Italy

[73] Assignee: Snamprogetti, S.p.A., Milan, Italy

[21] Appl. No.: 703,121

[22] Filed: July 6, 1976

[30] Foreign Application Priority Data

July 8, 1975 Italy .................................... 25171/75

[51] Int. Cl.$^2$ ............................................. C07C 11/02
[52] U.S. Cl. ........................ 260/677 A; 260/681.5 C; 560/242
[58] Field of Search ............. 260/498, 677 A, 681.5 R

[56] References Cited

U.S. PATENT DOCUMENTS

| | | | |
|---|---|---|---|
| 3,201,357 | 8/1965 | Fang et al. | 260/498 |
| 3,287,402 | 11/1966 | Landis | 260/498 |

Primary Examiner—C. Davis
Attorney, Agent, or Firm—Morgan, Finnegan, Pine, Foley & Lee

[57] ABSTRACT

A method is disclosed for removing the small fractions of acetylenic compounds from a mixed hydrocarbon stream, the improvement consisting in that said stream is treated with an organic acid in the presence of an acidic ion-exchange resin, preferably an —SO$_3$H containing resin, the acidic groups of said resin having totally been exchanged with alkali metal ions or alkaline earth metal ions. Acetic acid (glacial, anhydrous) is the preferred acid.

15 Claims, No Drawings

PROCESS FOR THE ADDITION OF ORGANIC ACIDS TO ACETYLENIC COMPOUNDS CONTAINED IN INORGANIC OR ORGANIC HYDROCARBON STREAMS

This invention relates to a method for the addition of organic acids to acetylenic compounds as contained in inorganic or organic hydrocarbon streams.

More particularly, the present invention relates to a method which permits both to purify the hydrocarbon streams and to exploit the acetylenic compounds in order concurrently to produce commercially interesting products.

Still more detailedly, the present invention relates to a method intended to:

1. removing acetylene from ethylene streams (either alone or in admixture with ethane and/or incondensable gases) and concurrently producing vinyl acetate;
2. removing propyne, 1-butyne, 2-butyne, vinyl-acetylene and diacetylene from hydrocarbon streams composed by ethylene, propylene and butadiene, both alone and in admixture with other saturated and/or unsaturated hydrocarbons having the same number of carbon atoms as acetylene, and concurrently producing vinyl-esters and/or gem-diesters of same acetylenic compounds;
3. removing propyne from a hydrocarbon stream composed by propylene, either alone or in admixture with other saturated and/or unsaturated hydrocarbons having the same number of carbon atoms, and concurrently producing the corresponding vinyl ester and/or gem-diester;
4. removing propyne, 1-butyne, 2-butyne, vinyl acetylene and diacetylene from a hydrocarbon stream composed by butadiene, either alone or in admixture with other saturated and/or unsaturated hydrocarbons having the same number of carbon atoms and obtaining the corresponding vinyl esters and/or gem-diesters.

It is known that in the majority of their practical uses, the saturated hydrocarbons, the olephins and dienes in particular must be free of acetylenic compounds. For example, the contents of acetylene in ehtylene must be, at the most, 1 part per million, due to the poisoning action and detrimental side reactions which can be originated in the catalysts used in the reactions intended to produce chemical compounds with ethylene and polyethylene as the statting materials.

A number of methods have been proposed and are used nowadays for removing acetylene from ehtylene, such as:

a. selective hydrogenation
b. extractive distillation in the presence of appropriate solvents.

These methods, and especially the first, permit that the required percentage of acetylene be attained in ethylene, but they require considerably high running costs and the loss of a certain percentage of ethylene. Similar considerations are true as to the stripping with conventional means of acetylene compounds from any hydrocarbon admixture which contains them.

It has been found that it is possible to do away in a complete manner with the drawbacks of te prior art by resorting, with a simple and cheap procedure, to the addition of organic acids to acetylenic compounds.

An object of the present invention is to provide a method which comprises the step of selectively adding to the acetylenic compounds which are contained in a hydrocarbon stream, both inorganic and organic, and organic acid, more particularly and preferably acetic acid, in the presence of an acidic ion-exchange resin the centers of which have totally been exchanged both with mercuric ions ($Hg^{++}$ ions) and ions of alkali metal or alkaline earth metals ($Me^{n+}$) ions.

More particularly, the present invention provides for the stripping of acetylene, as contained in a hydrocarbon stream in general, both inorganic and organic, by selective addition to it, either in the liquid or the vapor phase thereto, of acetic acid, by operating in the presence of an ion-exchange resin which contains both mercuric ions and sodium ions.

The as-formed esters are subsequently removed and recovered by simple and cheap rectification runs.

The ion-exchange resin used, as outlined above, has an acidic nature and it preferably contains sulphonic acid groups ($-SO_3H$ supported on resins, preferably polystyrene, divinylbenzene or polyphenolic resins and admixture thereof), but also resins which contain the $-COOH$ groups can be used, these being preferably supported on acrylate resins.

As a rule, the mercuric ions can be added to the resin in the form of their salts, more particularly and preferably in the form of mercury nitrate or acetate; the content of $Hg^{30+}$ ions of the resin will be anyhow slightly below the overall cationic capacity of the resin. The acidic groups of the resin, which have not been neutralized by mercuric ions, are neutralized with sodium ions or with ions of alkali metal or alkaline earth metals, these being added to the resin in the form of salts of such ions, but also hydroxides can be used to such a purpose. The contents of $Hg^{++}$ ions of the resin could be higher than that of the $Me^{n+}$ ions.

In order to neutralize the resin, it is preferred to use aqueous solutions, the resin being dehydrated, on completion of the treatments, for example by washing with anhydrous methanol. Subsequently, the resin shall be washed with the acid to be used in the reaction, said acid being compulsorily anhydrous.

The addition reaction can be carried out within a wide temperature and pressure range: it is an advantage to operate between 20° C and 120° C, and a shade better between 50° C and 80° C, under a pressure to be selected in such a way as to keep the hydrocarbon streams concerned in the liquid or the vapor phase at the reaction temperature, consistently with the advisability of treating such streams in the liquid or the vapor phase. More specifically, for acetylene in ethylene, the reaction of esterification with acetic acid (glacial) is performed in the vicinity of the boiling point temperature of vinyl acetate.

When operating in the gaseous phase, the spatical velocity (V/V/h), in terms of gas volume by catalyst volume per hour, of the reaction, is preferably, but not compulsorily, comprised between 7.5 and 30 (liters/-liters/hour). The run is carried out in the presence of a slight excess of the acid over the stoichiometric amount relative to the acetylene as contained in the stream to be processed, after that the resin has been thoroughly soaked by the acid.

It is interesting to note that, by operating according to the teaching of the present invention, the resin which has been totally exchanged with both mercuric ions on the one hand, and alkali metal ions or alkaline earth metals on the other hand, retains its activity over a period of time which is at least three times longer than that of the resin devoid of ions of alkali metals or alkaline earth metals. Presumably, this is also due to the fact that, with the resin treated according to the present invention, the side reactions, which generally take place in the presence of acidic ion-exchange resins, play a less prominent role.

A few examples will now be given, which are intended better to illustrate the invention without, however, limiting it in any wise.

EXAMPLE 1

150 grams of an Amberlyst 15 resin, containing acidic groups of the $—SO_3H$ type are added to 600 mls of a 3% aqueous solution of $Hg(NO_3)_2.H_2O$ (weight basis). The mixture is kept stirred during one hour, washed with demineralized water and treated with 1,300 mls of a 5% solution of sodium bicarbonate is demineralized water and stirred during an additional hour. A filtration under vacuum is carried out and the resin is subsequently washed with water, anhydrous methanol and then with glacial acetic acid until methanol has been discharged.

A portion of the thusly treated resin (120 grams) is placed in a jacketed reactor and is soaked with anhydrous glacial acetic acid.

The gas to be purified is caused to flow through the reactor at a spatial velocity, V/V/h, which is caused to vary.

The temperature is maintained in a range from 55° C to 75° C. The composition of the incoming gas is as follows;

ethylene — 98.07 molar %
acetylene — 1.93 molar %

From the contents of acetylene, as determined on the purified gas at the reactor outlet, and after having removed vinyl acetate by cooling, during a time of 10 hours, reading being taken at one-hour intervals, the following conversion percentages have been found:

| Temperature 55° C | | | | |
| --- | --- | --- | --- | --- |
| V/V/h (litres/litres/hour) | 7.5 | 15 | 20 | 30 |
| Acetylene conversion, % | 100.0 | 100.0 | 99.6 | 97.9 |
| Temperature 65° C | | | | |
| V/V/h (litres/litres/hour) | 7.5 | 15 | 20 | 30 |
| Acetylene conversion, % | 100.0 | 100.0 | 99.7 | 98.2 |
| Temperature 75° C | | | | |
| V/V/h (litres/litres/hour) | 7.5 | 20 | 30 | 40 |
| Acetylene conversion, % | 100.0 | 100.0 | 100.0 | 99.2 |

What we claim is:

1. A method for the removal of acetylenic compounds contained in inorganic or organic hydrocarbon streams, characterized in that an organic acid is added to said acetylenic compounds in the presence of an acidic ion-exchange resin, the acidic groups of which have been totally exchanged with both mercuric ions and ions of alkali metal or alkaline earth metals.

2. A method according to claim 1, wherein the acidic ion-exhange resin contains sulphonic acid groups ($—SO_3H$) before it is exchanged with mercuric ions and ions of alkali metals or alkaline earth metals.

3. A method according to claim 2, wherein the sulphonic acid groups are supported on polystyrene, phenolic, divinylbenzene resins or admixtures thereof.

4. A method according to claim 1, wherein the acidic ion-exchange resin contains carboxyl groups ($—COOH$) before it is exchanged with mercuric ions of alkali of alkali with metals.

5. A method according to claim 4, wherein the carboxyl groups are supported on acrylate resins.

6. A method according to claim 1, wherein the mercuric ions are added to the resins in the form of mercury salts.

7. A method according to claim 6, wherein the mercury salts are selected from the group consisting of mercury nitrate and mercury acetate.

8. A method according to claim, 1 wherein the ions of the alkali metals, or alkaline earth metals are added to the resin in the form of their salts or hydroxides.

9. A method according to claims, 1 wherein the reaction is carried out at a temperature ranging between 20° C and 120° C.

10. A method according to claim, 1, wherein the addition reaction is carried out in the liquid phase.

11. A method according to claim 1, wherein the addition reaction is carried out in the gaseous phase.

12. A method for the stripping of acetylene, propyne, 1-butyne, 2-butyne, vinylacetylene and diacetylene from a hydrocarbon stream composed by ethylene, propylene and butadiene, either alone or admixed with other saturated and/or unsaturated hydrocarbons having the same number of carbon atoms, characterized in that said stripping is carried out by a reaction according to claim 1, and the vinyl esters and/or the gem-diesters thus obtained are removed by rectification.

13. A method for stripping acetylene from a hydrocarbon stream composed by ethylene, either alone or admixed with ethane and/or uncondensable gases, characterized in that said stripping is carried out by a reaction of addition according to claim 1 and the vinyl ester an/or the gem-diester thus obtained are them removed by rectification.

14. A method for removing propyne from a hydrocarbon stream composed by propylene alone or admixed with other saturated and/or unsaturated hydrocarbons having the same number of carbon atoms, characterized in that said removal is carried out by an addition reaction according to claims 1 and the obtained vinyl ester and/or gem-diester is then removed by rectification.

15. A method for removing propyne, 1-butyne, 2-butyne, vinylacetylene, diacetylene from a hydrocarbon stream composed by butadiene either alone or in admixture with other saturated and/or unsaturated hydrocarbons having the same number of carbon atoms, characterized in that said removal is carried out by an addition reaction according to claim 1 and thus obtained vinyl esters and/or gem-diesters are subsequently removed by rectification.

* * * * *